United States Patent [19]

Nolte et al.

[11] Patent Number: 5,464,625
[45] Date of Patent: Nov. 7, 1995

[54] NON-TOXIC METHODS OF REPELLING RODENTS FROM MATERIALS SUSCEPTIBLE TO RODENT CONSUMPTION

[75] Inventors: Dale L. Nolte, Philadelphia, Pa.; J. Russell Mason, Bridgeton; Larry Clark, Salem, both of N.J.

[73] Assignee: Monell Chemical Senses Center, Philadelphia, Pa.

[21] Appl. No.: 137,948

[22] Filed: Oct. 15, 1993

Related U.S. Application Data

[63] Continuation of Ser. No. 880,512, May 8, 1992, abandoned.
[51] Int. Cl.$^6$ .................................................. A01N 25/02
[52] U.S. Cl. ..................... 424/405; 424/408; 424/409; 424/410; 424/411; 424/412; 514/920
[58] Field of Search ..................... 424/405, 408–412; 514/644–646, 741, 920

[56] References Cited

U.S. PATENT DOCUMENTS

| | | | |
|---|---|---|---|
| 1,999,458 | 4/1935 | Hollister | 424/411 |
| 3,663,253 | 5/1972 | Stone | 106/204 |
| 3,683,090 | 8/1973 | Henry et al. | 424/293 |
| 4,079,131 | 3/1978 | Lin et al. | 424/227 |
| 4,190,734 | 2/1980 | Dressler, Jr. | 174/38 |
| 4,542,162 | 9/1985 | Rutherford et al. | 521/79 |
| 4,735,803 | 4/1988 | Kate et al. | 424/195.1 |
| 4,790,990 | 12/1988 | Mason et al. | 424/438 |
| 5,085,868 | 2/1992 | Mattson et al. | 424/490 |

FOREIGN PATENT DOCUMENTS

| 1115410 | 5/1968 | United Kingdom | 424/405 |
|---|---|---|---|

OTHER PUBLICATIONS

Mason, et al.: Ortho–Aminoacetophenohe–Birds J. Wildl. Manage. 55(2) 334–340.
Schafer et al: Acute Oraltoxicity . . . Deer Mice Arch. Environ. Contam. Toxico. 14, 111–129 (1985).
Brooks et al.: Training Manual on Vertebrate Pest Mgmt. Pa Kistan Agricultural Research Council, 1990.
Salmon, T. P., "Evaluating rodenticide use impacts on agricultural production," *Vertebrate Pest Control and Management Materials*, 5th vol., pp. 115–127, Shumake and Bullard eds., Amercian Society for Testing and Materials, Philadelphia, Pa. (1988).
Marsh, R. E., "Rodent problems on the North American continent," *Rodent Pest Management*, pp. 1–12, I. Prakash ed., CRC Press Inc., Boca Raton, Fla. (1988).
Brooks, et al., *A Training Manual on Vertebrate Pest Management*, p. 206, Pakistan Agricultural Research Council, Islamadad, Pakistan (1990).

(List continued on next page.)

*Primary Examiner*—Thurman K. Page
*Assistant Examiner*—Neil Levy
*Attorney, Agent, or Firm*—Woodcock, Washburn, Kurtz, Mackiewicz & Norris

[57] ABSTRACT

Methods of effectively repelling vertebrates, especially rodents, from consuming or utilizing materials otherwise susceptible to such consumption or utilization, using at least one non-toxic rodent repellent compound selected from the group comprising acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methylanthranilate, ortho-aminoacetophenone, ortho-hydroxyacetophenone, ortho-methoxyacetophenone, para-aminoacetophenone, para-hydroxyacetophenone, para-methoxyacetophenone, and veratryl amine, are provided herein. Certain embodiments of the present invention relate to materials and methods for reducing crop damage, feedlot depredation, and livestock disease attributed to rodent infestation. Certain other embodiments relate to methods of decreasing rodent predation, especially predation of trees, in particular, seedlings. Other embodiments relate to methods of decreasing rodent utilization of functional articles such as telephone and electrical cables, refuse containers and the like. Rodent repellent compositions are also provided by this invention.

23 Claims, 14 Drawing Sheets

OTHER PUBLICATIONS

Castrale, "Impacts of conservation tillage practices on farmland wildlife in southeastern Indiana," *Indiana Statewide Wildlife Research Report no. W–26–R–18*, p. 28 (1987).

Gratz, "Rodents and human disease: a global appreciation," *Rodent Pest Management*, pp. 101–170, I. Prakash, ed., CRC Press Inc., Boca Raton, Fla. (1988).

Timm, "An IPM approach to rodent control on midwestern farms," *Proceedings of the Tenth Vertebrate Conference*, pp. 147–150, R. E. Marsh ed., Univ. of Calif., Davis (1982).

Campbell, et al., "Evaluation of BGR–P repellent to protect Douglas–fir seedlings from damage by mountain beavers," USDA, APHIS, Denver Wildlife Research Center, Special Report, Olympia, Wash. (1987).

Szolscanyi, J. et al., "Nociception in pigeons is not impaired by capsaicin," *Pain* 27:247–260 (1986).

Mason, J. R., et al., "Exploitable characteristics of neophobia and food aversions for improvements in rodent and bird control," pp. 20–39, D. E. Kaukienen, ed. *Vertebrate pest control and management materials*, Am. Soc. for Testing and Materials, Philadelphia, Pa. 315 pp (1983).

Meehan, "Chemical repellents," *Rodent Pest Management*, pp. 399–406, I. Prakash ed., CRC Press Inc., Boca Raton, Fla. (1988).

Mason, et al., "Ortho–aminoacetophenone repellency to birds: similarities to methyl anthranilate," *J. Wilde. Management* 55:334–40 (1991).

Clark and Shah, "Nonlethal bird repellents: in search of a general model relating repellency and chemical structure," *J. Wildl. Management* 55:538–45 (1991).

Clark, et al., "Chemical repellency in birds; relationship between chemical structure and avoidance response," *J. Exp. Zoology* 260:310–22 (1991).

Beauchamp and Mason, "Comparative hedonics of taste," *The Hedonics of Taste*, pp. 159–183, Bolles ed., Lawrence Erlbaum Assoc., Hillsdale, N.J. (1991).

Mason, J. R., et al., "Taxonomic differences between birds and mammals in their responses to chemical irritants," D. Mullen–Schwarze, et al. eds. *Chemical Signals in Vertebrates*, VI, Plenum Press, NY, N.Y., (1991).

FIG. 2A

| Acetophenone | | | n=10 | | | |
|---|---|---|---|---|---|---|
| PRETREATMENT | Day 1 | Day 2 | Day 3 | Day 4 | Mean | C.I. |
| Mean | 4.06 | 3.80 | 3.96 | 4.16 | 4.00 | 3.49<X<4.21 |
| se | .31 | .27 | .22 | .22 | .23 | |
| TREATMENT | Day 1 | Day 2 | Day 3 | Day 4 | Mean | C.I. |
| Mean | 0.90 | 0.90 | 2.85 | 2.29 | 1.76 | 2.26<X<3.42 |
| se | .36 | .27 | .31 | .15 | .19 | |

FIG. 2B

| 2-aminobenzyl alcohol | | | n=10 | | | |
|---|---|---|---|---|---|---|
| PRETREATMENT | Day 1 | Day 2 | Day 3 | Day 4 | Mean | C.I. |
| Mean | 4.42 | 4.82 | 4.11 | 4.25 | 4.15 | 3.69<X<4.61 |
| se | .69 | .59 | .32 | .30 | .28 | |
| TREATMENT | Day 1 | Day 2 | Day 3 | Day 4 | Mean | C.I. |
| Mean | 0.44 | 0.78 | 0.42 | 0.30 | 0.50 | 0.37<X<0.63 |
| se | .12 | .24 | .10 | .13 | .08 | |

FIG. 2C

| 2-amino-4'5'-dimethoxyacetophenone | | | n=10 | | | |
|---|---|---|---|---|---|---|
| PRETREATMENT | Day 1 | Day 2 | Day 3 | Day 4 | Mean | C.I. |
| Mean | 4.93 | 4.21 | 4.64 | 4.55 | 4.58 | 3.49<X<4.31 |
| se | .58 | .21 | .36 | .41 | .26 | |
| TREATMENT | Day 1 | Day 2 | Day 3 | Day 4 | Mean | C.I. |
| Mean | 1.05 | 1.43 | 1.36 | 1.28 | 1.28 | 2.20<X<2.89 |
| se | .15 | .33 | .22 | .23 | .16 | |

FIG. 2D

| Anthranilamide | n=10 | | | | | |
|---|---|---|---|---|---|---|
| PRETREATMENT | Day 1 | Day 2 | Day 3 | Day 4 | Mean | C.I. |
| Mean | 3.73 | 4.09 | 4.02 | 4.20 | 4.01 | 3.81<X<4.21 |
| se | .14 | .20 | .19 | .17 | .12 | |
| TREATMENT | Day 1 | Day 2 | Day 3 | Day 4 | Mean | C.I. |
| Mean | 1.62 | 1.65 | 3.02 | 1.76 | 2.01 | 1.73<X<2.29 |
| se | .20 | .13 | .46 | .16 | .17 | |

FIG. 2E

| Anthranilic acid | n=10 | | | | | |
|---|---|---|---|---|---|---|
| PRETREATMENT | Day 1 | Day 2 | Day 3 | Day 4 | Mean | C.I. |
| Mean | 3.73 | 3.81 | 3.86 | 4.00 | 3.85 | 3.49<X<4.21 |
| se | .47 | .21 | .17 | .20 | .22 | |
| TREATMENT | Day 1 | Day 2 | Day 3 | Day 4 | Mean | C.I. |
| Mean | 2.56 | 3.42 | 3.01 | 2.37 | 2.84 | 2.26<X<3.42 |
| se | .62 | .68 | .18 | .19 | .35 | |

FIG. 2F

| Isatoic anhydride | n=10 | | | | | |
|---|---|---|---|---|---|---|
| PRETREATMENT | Day 1 | Day 2 | Day 3 | Day 4 | Mean | C.I. |
| Mean | 3.91 | 3.78 | 4.15 | 4.19 | 4.01 | 3.80<X<4.22 |
| se | .18 | .16 | .15 | .15 | .13 | |
| TREATMENT | Day 1 | Day 2 | Day 3 | Day 4 | Mean | C.I. |
| Mean | 3.07 | 4.32 | 3.67 | 3.24 | 3.58 | 3.30<X<3.86 |
| se | .27 | .32 | .18 | .23 | .17 | |

FIG. 2G

| Isobutyl anthranilate | | | n=10 | | | |
|---|---|---|---|---|---|---|
| PRETREATMENT | Day 1 | Day 2 | Day 3 | Day 4 | Mean | C.I. |
| Mean | 3.37 | 4.28 | 3.84 | 4.10 | 3.90 | 3.49<X<4.31 |
| se | .54 | .33 | .19 | .16 | .25 | |
| TREATMENT | Day 1 | Day 2 | Day 3 | Day 4 | Mean | C.I. |
| Mean | 1.62 | 3.24 | 2.85 | 2.45 | 2.54 | 2.19<X<2.89 |
| se | .32 | .42 | .11 | .30 | .21 | |

FIG. 2H

| 4-ketobenztriazine | | | n=10 | | | |
|---|---|---|---|---|---|---|
| PRETREATMENT | Day 1 | Day 2 | Day 3 | Day 4 | Mean | C.I. |
| Mean | 4.31 | 4.30 | 4.30 | 4.38 | 4.32 | 3.71<X<4.93 |
| se | .52 | .32 | .55 | .26 | .37 | |
| TREATMENT | Day 1 | Day 2 | Day 3 | Day 4 | Mean | C.I. |
| Mean | 1.23 | 1.65 | 1.46 | 1.34 | 1.42 | 0.68<X<2.16 |
| se | .16 | .37 | .37 | .34 | .45 | |

FIG. 2I

| Meta-aminoacetophenone | | | n=8 | | | |
|---|---|---|---|---|---|---|
| PRETREATMENT | Day 1 | Day 2 | Day 3 | Day 4 | Mean | C.I. |
| Mean | 4.55 | 4.63 | 5.23 | 4.98 | 4.84 | 4.35<X<5.33 |
| se | .34 | .31 | .32 | .38 | .30 | |
| TREATMENT | Day 1 | Day 2 | Day 3 | Day 4 | Mean | C.I. |
| Mean | 1.43 | 0.79 | 0.65 | 0.63 | 0.87 | 0.67<X<1.07 |
| se | .10 | .15 | .17 | .18 | .12 | |

FIG. 2J

| Meta-hydroxyacetophenone | | | | n=8 | | |
|---|---|---|---|---|---|---|
| PRETREATMENT | Day 1 | Day 2 | Day 3 | Day 4 | Mean | C.I. |
| Mean | 4.78 | 4.98 | 5.68 | 5.03 | 5.11 | 4.60<X<5.62 |
| se | .34 | .34 | .49 | .31 | .31 | |
| TREATMENT | Day 1 | Day 2 | Day 3 | Day 4 | Mean | C.I. |
| Mean | 3.63 | 2.78 | 2.75 | 3.15 | 3.08 | 2.49<X<3.67 |
| se | .55 | .54 | .28 | .23 | .36 | |

FIG. 2K

| Meta-methoxyacetophenone | | | | n=8 | | |
|---|---|---|---|---|---|---|
| PRETREATMENT | Day 1 | Day 2 | Day 3 | Day 4 | Mean | C.I. |
| Mean | 4.83 | 4.45 | 4.33 | 4.30 | 4.48 | 4.12<X<4.84 |
| se | .25 | .16 | .26 | .25 | .22 | |
| TREATMENT | Day 1 | Day 2 | Day 3 | Day 4 | Mean | C.I. |
| Mean | 3.45 | 3.40 | 3.43 | 3.43 | 3.43 | 3.10<X<3.76 |
| se | .28 | .18 | .20 | .21 | .20 | |

FIG. 2L

| 2-methoxybenzoic acid | | | | n=10 | | |
|---|---|---|---|---|---|---|
| PRETREATMENT | Day 1 | Day 2 | Day 3 | Day 4 | Mean | C.I. |
| Mean | 3.24 | 4.24 | 4.18 | 4.29 | 3.99 | 3.63<X<4.35 |
| se | .54 | .23 | .24 | .24 | .25 | |
| TREATMENT | Day 1 | Day 2 | Day 3 | Day 4 | Mean | C.I. |
| Mean | 2.16 | 2.88 | 2.93 | 3.22 | 2.80 | 2.44<X<3.16 |
| se | .31 | .18 | .33 | .56 | .22 | |

FIG. 2M

| Methyl anthranilate | | n=10 | | | | |
|---|---|---|---|---|---|---|
| PRETREATMENT | Day 1 | Day 2 | Day 3 | Day 4 | Mean | C.I. |
| Mean | 3.52 | 3.86 | 3.66 | 3.86 | 3.73 | 3.35<X<4.11 |
| se | .58 | .22 | .19 | .14 | .23 | |
| TREATMENT | Day 1 | Day 2 | Day 3 | Day 4 | Mean | C.I. |
| Mean | 0.35 | 2.67 | 2.43 | 2.92 | 2.09 | 1.53<X<2.65 |
| se | .16 | .53 | .25 | .79 | .34 | |

FIG. 2N

| Methyl cinnamate | | n=10 | | | | |
|---|---|---|---|---|---|---|
| PRETREATMENT | Day 1 | Day 2 | Day 3 | Day 4 | Mean | C.I. |
| Mean | 4.40 | 5.03 | 4.92 | 4.65 | 4.75 | 3.98<X<5.47 |
| se | .53 | .47 | .59 | .50 | .47 | |
| TREATMENT | Day 1 | Day 2 | Day 3 | Day 4 | Mean | C.I. |
| Mean | 3.42 | 5.77 | 4.01 | 4.85 | 4.51 | 3.98<X<5.04 |
| se | .24 | .67 | .15 | .59 | .32 | |

FIG. 2O

| Methyl salicylate | | n=10 | | | | |
|---|---|---|---|---|---|---|
| PRETREATMENT | Day 1 | Day 2 | Day 3 | Day 4 | Mean | C.I. |
| Mean | 3.55 | 3.40 | 3.83 | 3.95 | 3.68 | 3.37<X<3.99 |
| se | .15 | .39 | .22 | .20 | .19 | |
| TREATMENT | Day 1 | Day 2 | Day 3 | Day 4 | Mean | C.I. |
| Mean | 1.60 | 4.01 | 3.99 | 3.67 | 3.32 | 3.11<X<3.53 |
| se | .45 | .60 | .25 | .10 | .13 | |

FIG. 2P

| Ortho-aminoacetophenone | | | | n=8 | | |
|---|---|---|---|---|---|---|
| PRETREATMENT | Day 1 | Day 2 | Day 3 | Day 4 | Mean | C.I. |
| Mean | 4.30 | 4.63 | 4.35 | 4.53 | 4.45 | 4.12<X<4.78 |
| se | .19 | .25 | .24 | .20 | .20 | |
| TREATMENT | Day 1 | Day 2 | Day 3 | Day 4 | Mean | C.I. |
| Mean | 0.08 | 0.20 | 1.23 | 0.45 | 0.49 | 0.01<X<0.97 |
| se | .04 | .12 | .67 | .40 | .29 | |

FIG. 2Q

| Ortho-hydroxyacetophenone | | | | n=8 | | |
|---|---|---|---|---|---|---|
| PRETREATMENT | Day 1 | Day 2 | Day 3 | Day 4 | Mean | C.I. |
| Mean | 4.55 | 4.70 | 4.43 | 4.33 | 4.50 | 4.19<X<4.81 |
| se | .20 | .36 | .22 | .19 | .19 | |
| TREATMENT | Day 1 | Day 2 | Day 3 | Day 4 | Mean | C.I. |
| Mean | 2.23 | 1.75 | 2.53 | 2.45 | 2.24 | 2.01<X<2.47 |
| se | .29 | .34 | .27 | .35 | .14 | |

FIG. 2R

| Ortho-methoxyacetophenone | | | | n=8 | | |
|---|---|---|---|---|---|---|
| PRETREATMENT | Day 1 | Day 2 | Day 3 | Day 4 | Mean | C.I. |
| Mean | 5.70 | 5.65 | 5.43 | 5.40 | 5.54 | 4.98<X<6.10 |
| se | .58 | .37 | .31 | .27 | .34 | |
| TREATMENT | Day 1 | Day 2 | Day 3 | Day 4 | Mean | C.I. |
| Mean | 2.05 | 2.55 | 2.88 | 3.13 | 2.65 | 2.32<X<2.98 |
| se | .20 | .28 | .22 | .24 | .20 | |

FIG. 2S

| Para-aminoacetophenone | | | n=8 | | | |
|---|---|---|---|---|---|---|
| PRETREATMENT | Day 1 | Day 2 | Day 3 | Day 4 | Mean | C.I. |
| Mean | 4.63 | 4.88 | 4.83 | 4.75 | 4.77 | 4.26<X<5.28 |
| se | .31 | .26 | .45 | .33 | .31 | |
| TREATMENT | Day 1 | Day 2 | Day 3 | Day 4 | Mean | C.I. |
| Mean | 1.70 | 1.18 | 1.10 | 0.30 | 1.07 | 0.89<X<1.25 |
| se | .09 | .20 | .18 | .08 | .11 | |

FIG. 2T

| Para-hydroxyacetophenone | | | n=8 | | | |
|---|---|---|---|---|---|---|
| PRETREATMENT | Day 1 | Day 2 | Day 3 | Day 4 | Mean | C.I. |
| Mean | 4.40 | 4.43 | 4.30 | 4.60 | 4.43 | 4.20<X<4.66 |
| se | .15 | .22 | .13 | .20 | .14 | |
| TREATMENT | Day 1 | Day 2 | Day 3 | Day 4 | Mean | C.I. |
| Mean | 3.15 | 2.75 | 2.60 | 2.80 | 2.83 | 2.63<X<3.03 |
| se | .21 | .12 | .14 | .19 | .12 | |

FIG. 2U

| Para-methoxyacetophenone | | | n=8 | | | |
|---|---|---|---|---|---|---|
| PRETREATMENT | Day 1 | Day 2 | Day 3 | Day 4 | Mean | C.I. |
| Mean | 4.65 | 4.80 | 4.68 | 4.75 | 4.72 | 4.34<X<5.10 |
| se | .25 | .27 | .22 | .20 | .23 | |
| TREATMENT | Day 1 | Day 2 | Day 3 | Day 4 | Mean | C.I. |
| Mean | 3.60 | 3.30 | 3.33 | 3.10 | 3.33 | 2.79<X<3.87 |
| se | .46 | .37 | .38 | .33 | .33 | |

FIG. 2V

| Phenethyl anthranilate | | n=10 | | | | |
|---|---|---|---|---|---|---|
| PRETREATMENT | Day 1 | Day 2 | Day 3 | Day 4 | Mean | C.I. |
| Mean | 3.27 | 4.04 | 3.99 | 3.90 | 3.80 | 3.54<X<4.06 |
| se | .17 | .17 | .24 | .19 | .16 | |
| TREATMENT | Day 1 | Day 2 | Day 3 | Day 4 | Mean | C.I. |
| Mean | 3.28 | 4.57 | 4.29 | 3.89 | 4.01 | 3.80<X<4.22 |
| se | .31 | .26 | .18 | .10 | .13 | |

FIG. 2W

| Sodium benzoate | | n=10 | | | | |
|---|---|---|---|---|---|---|
| PRETREATMENT | Day 1 | Day 2 | Day 3 | Day 4 | Mean | C.I. |
| Mean | 3.00 | 3.97 | 3.97 | 4.08 | 3.76 | 3.58<X<3.94 |
| se | .50 | .15 | .11 | .15 | .11 | |
| TREATMENT | Day 1 | Day 2 | Day 3 | Day 4 | Mean | C.I. |
| Mean | 2.89 | 3.52 | 3.56 | 3.97 | 3.49 | 3.28<X<3.70 |
| se | .27 | .22 | .14 | .20 | .13 | |

FIG. 3

| | PRAIRIE VOLES | |
|---|---|---|
| | Pretreatment | Treatment |
| OAP | 7.6 | 0.6 |
| AMAP | 8.1 | 4.8 |
| MA | 7.8 | 5.3 |

FIG. 4

| | RATS | |
|---|---|---|
| | Pretreatment | Treatment |
| OAP | 28.2 | 0.6 |

FIG. 5

| Chemical | Concentration | Period | Concentration x Period |
|---|---|---|---|
| Amino | | | |
| Ortho-amino-acetophenone | $F$ = 4.1; 2,21 df; $P$ < 0.03 | $F$ = 393.4; 1,21df; $P$ < 0.00001 | NS |
| Meta-amino-acetophenone | NS | $F$ = 501.6; 1,21df; $P$ < 0.00001 | NS |
| Para-amino-acetophenone | NS | $F$ = 461.6; 1,21df; $P$ < 0.00001 | NS |
| Methoxy | | | |
| Ortho-methoxy-acetophenone | $F$ = 7.3; 2,21 df; $P$ < 0.004 | $F$ = 326.5; 1,21df; $P$ < 0.00001 | $F$ = 46.0; 2,21df; $P$ < 0.00001 |
| Meta-methoxy-acetophenone | $F$ = 9.2; 2,21df; $P$ < 0.002 | $F$ = 123.3; 1,21df; $P$ < 0.00001 | $F$ = 36.3; 2,21df; $P$ < 0.00001 |
| Para-methoxy-acetophenone | $F$ = 6.1; 2,21df; $P$ < 0.008 | $F$ = 122.4; 1,21df; $P$ < 0.00001 | $F$ = 31.2; 2,21df; $P$ < 0.00001 |
| Hydroxy | | | |
| Ortho-hydroxy-acetophenone | $F$ = 6.6; 2,21df; $P$ < 0.006 | $F$ = 215.2; 1,21df; $P$ < 0.00001 | $F$ = 15.4; 2,21df; $P$ < 0.0002 |
| Meta-hydroxy-acetophenone | $F$ = 8.1; 2,21df; $P$ < 0.006 | $F$ = 101.4; 1,21df; $P$ < 0.00001 | $F$ = 21.9; 2,21df; $P$ < 0.0002 |
| Para-hydroxy-acetophenone | $F$ = 7.1; 2,21df; $P$ < 0.006 | $F$ = 147.3; 1,21df; $P$ < 0.00001 | $F$ = 14.3; 2,21df; $P$ < 0.0003 |
| | | | |

NON-TOXIC METHODS OF REPELLING RODENTS FROM MATERIALS SUSCEPTIBLE TO RODENT CONSUMPTION

GOVERNMENT SUPPORT

This invention was made with Government support. The U.S. Government may have certain rights in this invention. This is a continuation of U.S. application Ser. No. 07/880,512 filed May 8, 1992, now abandoned.

FIELD OF THE INVENTION

This invention relates to the field of rodent repellency, especially non-toxic methods of repelling rodents.

BACKGROUND OF THE INVENTION

There is a continuing effort to develop novel methods for reducing agricultural losses. Significant loss may be attributed to vertebrates, for example, rodents. Although limited data are available that document the distribution and magnitude of agricultural losses caused by vertebrates (Salmon, T. P., "Evaluating rodenticide use impacts on agricultural production," in *Vertebrate Pest Control and Management Materials*, 5th Vol., pages 115–127, Shumake and Bullard eds., American Society for Testing and Materials, Philadelphia, Pa. (1988)), such losses are believed to be substantial (Marsh, "Rodent problems on the North American continent," in *Rodent Pest Management*, pages 1–12, I. Prakash ed., CRC Press Inc., Boca Raton, Fla. (1988)), and damage is likely to increase in the future as conservation tillage practices become more widespread.

It is generally recognized that rodents, for example, rats (e.g., *Rattus norvegicus, Rattus rattus*), mice (e.g., *Mus musculus, Peromyscus maniculatus*), voles (e.g., *Pitymys pinetorum, Microtus pennsylvanicus*), and various ground squirrels (e.g., *Citellus* spp.), cause greater economic harm than other vertebrates. Brooks et al., *A Training Manual on Vertebrate Pest Management*, page 206, Pakistan Agricultural Research Council, Islamabad, Pakistan (1990); Castrale, "Impacts of conservation tillage practices on farmland wildlife in southeastern Indiana," *Indiana Statewide Wildlife Research Report* No. W-26-R-18, page 28 (1987). Significant losses to feed, forage, oil and fiber crops are attributed to rodent consumption before harvest, and harvested materials are further depleted by rodents during transportation and storage.

Rodents are also indirectly responsible for livestock loss to disease. Rodents serve as primary reservoirs or hosts to vectors for human and livestock diseases, including viral zoonoses (e.g., Venezuelan equine encephalitis), rickettsial diseases (e.g., Rocky mountain spotted fever) and bacterial diseases (e.g., salmonella). Gratz, "Rodents and human disease: a global appreciation," in *Rodent Pest Management*, Pages 101–170, I. Prakash, ed., CRC Press Inc., Boca Raton, Fla. (1988). Livestock loss to such diseases may be economically significant, and the potential for transmission to humans presents serious health concerns.

In addition to causing agricultural losses, commensal rodents are responsible for structural damage. Rodents undermine and weaken structures (Marsh, "Rodent problems on the North American continent," in *Rodent Pest Management*, page 1–12, I. Prakash ed., CRC Press Inc., Boca Raton, Fla. (1988); Timm, "An IPM approach to rodent control on midwestern farms," in *Proceedings of the Tenth Vertebrate Conference*, Pages 147–150, R. E. Marsh ed., Univ. of California, Davis (1982)), and chew through electrical and telephone cables. Rodents are particularly attracted to containers for discarded refuse, packaging, fabrics, and plastics.

Rodent predation of trees actually hinders reforestation efforts. Mountain beavers (*Aplodontia rufa*), hinder reforestation on more than 121,500 ha of otherwise highly productive land in the Pacific Northwest. Campbell and Evans, "Recent approaches to controlling mountain beavers (*Aplodontia rufa*) in Pacific Northwest forests," *Proc. Vertebr. Pest Conf.* 13:183–87, Davis, Calif. (1988). The most common form of damage is the cutting of seedlings. Clipped seedlings often die and those trees which do survive generally suffer retarded growth and deformities. Borrecco and Anderson, "Mountain beaver problems in the forests of California, Oregon and Washington," *Proc. Vertebr. Pest Conf.*, pages 135–42, Fresno, Calif. (1980). Further, mountain beavers will girdle adult trees and crop branches. The longevity of trees and the continuing need for protection makes them a difficult crop to safeguard from predation.

Various methods, for example, trapping (Evans, "Mountain beaver damage and management," *Proc Symp. Animal Damage Management in Pacific Northwest Forests*, pages 73–74, Spokane, Wash. (1987)), poisoning and mechanical barriers (Campbell and Evans, supra) have been used in an attempt to control rodent predation of trees. Likewise, habitat manipulation and the destruction of burrow systems has the potential to displace animals and thereby reduce predation. However, each of these methods is costly, and with the exception of poisoning, each is difficult to implement on a large scale.

Chemical repellents are generally preferred to mechanical barriers, in part, because chemical aversive agents may be employed on a large scale, relatively economically. Chemical agents, such as Big Game Repellent (BGR-P; fermented egg products), may be applied directly to the locus from which rodents are to be repelled. Mountain beaver damage to trees to which BGR-P was provided is significantly less than that inflicted on untreated trees. Campbell, et al., "Evaluation of BGR-P repellent to protect Douglas-fir seedlings from damage by mountain beavers," USDA APHIS Denver Wildlife Research Center, Special Report, Olympia, Wash. (1987). However, with the exception of Big Game Repellent (BGR-P), no such aversive chemicals have been available for use against rodents. Campbell, et al., supra.

Damage may be further reduced by providing the area around the trees with chemical repellents that make the area uninhabitable. For example, pocket gopher (*Thomomys talpoides*) avoid burrows that have been treated with predator odors. Sullivan, et al., "Use of predator odors as repellents to reduce feeding damage by herbivores III. Montane and meadow voles (*Microtus montanus* and *Microtus pennsylvanicus*)," *J. Chem. Ecol.* 14:363–78 (1988).

As a cost effective measure, chemical repellent treatments may be limited to seasons when damage is most likely to occur. For example, at high elevations Douglas fir are predominately taken during winter and spring when other forage is not readily available and the nutritional value of conifers is high. O'Brian, "Seasonal selection of coniferous trees by the sewellel *Aplodontia tufa*," *Mammalia* 52:325–30 (1988).

Chemical repellent agents may also be employed to decrease agricultural losses directly traceable to rodent consumption and to reduce the indirect losses attributed to rodent infestation, such as livestock loss to disease. Rodent utilization of functional articles, such as electrical and telephone cables, refuse containers, and the like, may be reduced by chemical rodent repellents. Such repellents may be applied directly to the locus from which rodents are to be repelled or to the area around the locus. Such repellents may also be incorporated in polymers for use in making the functional articles. Similarly, rodent utilization of other materials, in particular, trees, may be reduced by chemical rodent repellents. Such repellents may be applied directly to the trees, or to the area around the trees, for example, the rodent burrows. Chemical repellents may be used to prevent rodent infestation or preempt reinvasion. Selective application of chemical rodent repellent agents, for example, application during seasons when damage is most likely to occur, may be a cost effective method of reducing rodent utilization of materials susceptible to such utilization.

Feedlot depredation and livestock loss to disease may be reduced by decreasing rodent attraction to livestock feedlot and/or water supply, which may be measured as a reduction in rodent consumption of such provisions. There are a number of identified avian aversive agents that may be safely added to livestock feed without affecting the palatability of such feed. However, repellency in birds is substantially different than that in mammals. Szolscanyi, J., et al. "Nociception in pigeons is not impaired by capsaicin", *Pain* 27:247–260 (1986); Mason, J R , et al ,. "Exploitable characteristics of neophobia and food aversions for improvements in rodent and bird control", Pages 20–39 in D E. Kaukienen, ed. *Vertebrate pest control and management materials. Am. Soc.* for Testing and Materials, Philadelphia, Pa. 315pp (1983). Thus, although methyl anthranilate (MA), a known bird repellent agent is palatable to humans and livestock (Furia and Bellanca, *Handbook of flavor ingredients*, at page 346, CRC Press, Cleveland, Ohio (1975); Glahn, et al,. "Dimethyl anthranilate as a bird repellent in livestock feed," *Wildl Soc. Bull.* 17:31–320. 1989), research indicates that it is accepted by rodents such as deer mice. Schafer and Bowles, "Acute oral toxicity and repellency of 933 chemicals to house and deer mice." *Arch., Environ. Contam. Toxicol.* 14:111–129 (1985). Repellents like capsaicin or denatonium saccharide and denatonium benzoate are either broadly offensive to all mammals (Meehan, "Chemical repellents," in *Rodent Pest Management*, pages 399–406, I. Prakash ed., CRC Press Inc., Boca Raton, Fla. (1988)), or show considerable inter- and intra-specific variability in effectiveness, thus making their performance unpredictable.

At present, there are several substances that can act as rodent repellents, for example, capsaicin. However, these substances are generally either toxic or aversive to humans and domestic livestock. A promising strategy for the development of new rodent repellents may be molecular modelling where chemical structure is related to biological activity. This approach was used to test 36 derivatives of benzoic acids as bird repellents. Mason, et al., "Ortho-aminoacetophenone repellency to birds: similarities to methyl anthranilate," *J. Wildl. Management* 55:334–40 (1991); Clark and Shah, Nonlethal bird repellents: in search of a general model relating repellency and chemical structure," *J Wildl. Management* 55:538–45 (1991); Clark, et al., "Chemical repellency in birds; relationship between chemical structure and avoidance response," *J. Exp Zoology* 260:310–22 (1991). Three molecular features contribute to avian repellency: (1) the basicity of a substituted phenyl ring; (2) the presence of an electron-donating group in resonance with an electron withdrawing group on a phenyl ring; and (3) a heterocyclic ring in the same pi cloud plane as the phenyl ring, the ring comprised of an intramolecular hydrogen bond or covalently bonded heteroatoms. Clark and Shah, supra.

With reference to the foregoing, it is clear that there is a need for methods to reduce rodent consumption or utilization of materials susceptible to rodent consumption or utilization. In these methods, chemical aversive agents are generally preferred to mechanical means, and non-lethal chemical repellent agents are further preferred. In addition to the aforementioned utility, such non-toxic repellent agents may be used to reduce the health hazard granular agricultural chemicals present to rodents and birds that unwittingly ingest them. A non-toxic chemical agent which repels both rodents and birds and which may be included in the manufacture of hazardous agricultural chemicals would have considerable utility. At present, no such repellent exists. Beauchamp and Mason, "Comparative hedonics of taste," in The Hedonics of Taste, pages 159–183, Bolles ed., Lawrence Erlbaum Assoc., Hillsdale, N.J. (1991).

There is a need for non-toxic rodent repellent agents that may be added to livestock feed and/or water supply without affecting the palatability of such provisions. There is a further need for rodent repellent agents which may be used directly or indirectly to protect trees from predation and/or which may be applied to or incorporated into polymers used to make functional articles which are susceptible to being utilized or damaged by rodents. There is still a further need for non-toxic rodent repellent agents that may be applied to crops to decrease rodent consumption both before and after harvest. Heretofore, such non-toxic rodent repellents have not been available.

SUMMARY OF THE INVENTION

It has now been found that certain non-toxic compounds can be used to effectively repel vertebrates, especially rodents, from consuming or utilizing materials otherwise susceptible to consumption or utilization by rodents. The subject compounds include acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone, and veratryl amine. In accordance with the methods of the present invention, one or more of these compounds are added to or incorporated in livestock feed and/or water supply in amounts which are effective to provide the desired repellancy, without adversely affecting food and/or water palatability. In accordance with certain of the herein-described methods, crop damage, feedlot depredation, and livestock disease attributed to rodent infestation are markedly reduced. Other preferred methods effectively decrease rodent predation, especially predation of trees, in particular, seedlings. Other embodiments relate to methods of decreasing rodent utilization of functional articles such as telephone and electrical cables, refuse containers and the like. Rodent repellent compositions are also provided by this invention.

BRIEF DESCRIPTION OF THE DRAWINGS

FIGS. 2a–2w are a series of tables showing the mean (se) intake by mice of water (in ml) during a 4 day pretreatment period and subsequent intake of water containing a 0.5% weight/volume concentration of each compound during a treatment period. The 95% confidence intervals for each compound are also provided.

FIG. 3 is a table showing the average water intake (in ml) by prairie voles during a 4 day pretreatment period and subsequent intake of water containing ortho-aminoacetophenone (OAP), 2-amino-4'5'-dimethoxyacetophenone (AMAP) and methyl anthranilate (MA) during a treatment periods.

FIG. 4 is a table showing the average water intake (in ml) by rats during a 4 day pretreatment period and subsequent of water containing ortho-aminoacetophenone (OAP) during a treatment periods.

FIG. 5 is a table showing the concentration, period, and concentration x period interaction terms for analyses of Ortho-aminoacetophenone, meta-aminoacetophenone, para-aminoacetophenone, ortho-methoxyacetophenone, meta-methoxyacetophenone, para-methoxyacetophenone, ortho-hydroxyacetophenone, meta-hydroxyacetophenone and para-hydroxyacetophenone at concentrations of 1.0%, 0.5% and 0.25% (mass/vol or vol/vol). NS=not significant.

DETAILED DESCRIPTION OF THE INVENTION

Figure 1:
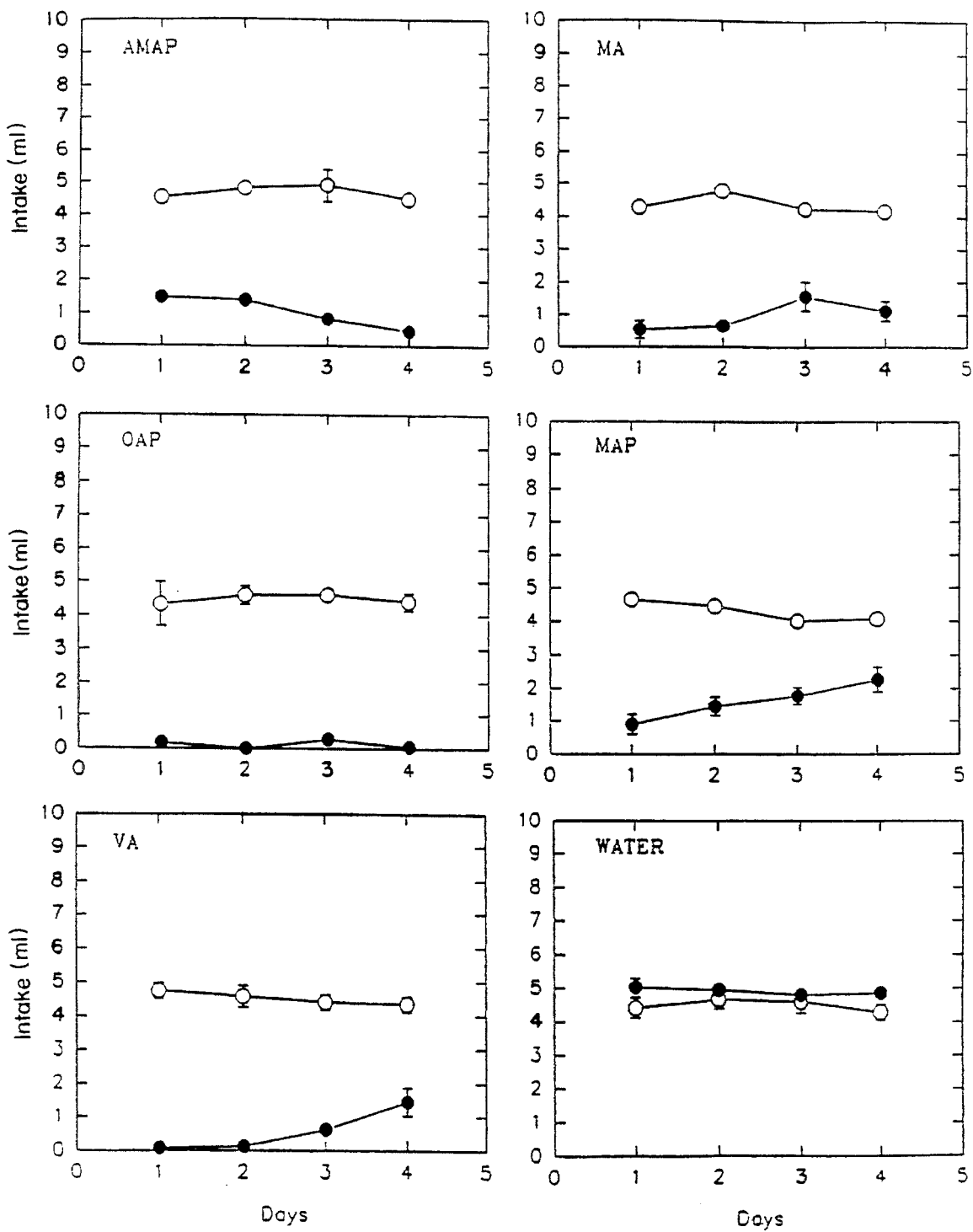
FIG. 1 is a series of graphs showing the intake by mice of water (in ml) during a 4 day pretreatment period (open circles) and subsequent intake of water containing a 1% weight/volume concentration of methyl anthranilate (MA) , ortho-aminoacetophenone (OAP), 2-amino-4'5'-dimethoxyacetophenone (AMAP), 2-methoxyacetophenone (MAP), veratryl amine (VA) and water (control) during a 4 day treatment period (darkened circles).

As used herein, the term "rodents" refers to members of the rodentia and lagomorpha orders, for example, squirrels (e.g., Sciurus spp.), rats (e.g., *Rattus norvegicus, Rattus rattus*), mice (e.g., *Mus musculus, Peromyscus maniculatus*), voles (e.g., *Pitymys pinetorum, Microtus pennsylvanicus*), ground squirrels (e.g., Citellus spp.), mountain beavers (*Aplodontia tufa*), pocket gopher (*Thomomys talpoides*), rabbits (e.g., Sylvilagus spp.), hares (e.g., Lepus spp.) and other lagomorphs and rodents.

Essentially, utilization refers to any contact a rodent may have with materials, especially contact which causes some destruction or diminution in value of said materials. Materials which may be utilized by rodents include containers for discarded refuse, packaging, fabrics, and plastics. Products or functional articles which may be damaged by rodent contact, for example, electrical and telephone cables which may be damaged by a rodent's gnawing, are also materials which may be utilized by rodents.

Materials which may be consumed by rodents include solid materials such as feedlot, seeds, and crops and liquid materials such as water. Other materials which may be consumed by rodents include agrichemicals such as pesticides and herbicides.

A compound or aversive agent is repellent if it substantially reduces rodent consumption or utilization of a material as compared to consumption or utilization of the same material in the absence of such repellent compound. Those of ordinary skill in the art will recognize methods of testing to determine the amount of compound which will provide the desired rodent-repellency effect.

Although not wishing to be bound by any particular mechanism of action, it is believed that rodents are repelled in the methods of this invention through sensory factors and/or conditioning based on post-ingestional malaise.

The non-toxic rodent repellent compounds of this invention may be selected from the group comprising acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone, and veratryl amine.

In the practice of the present invention, at least one of the compounds disclosed herein may be provided to the material from which rodents are to be repelled in any suitable manner. Certain methods of this invention comprise providing an effective amount of at least one rodent repellent composition to the locus from which rodents are to be repelled via a carrier. Suitable carriers for application may include liquid diluents and inert solid carriers. Said compositions may, for example, be provided in an emulsified form and sprayed onto the material. Alternatively, said compositions may be diluted in a liquid or at least partially encapsulated in an inert solid carrier. Carriers providing a controlled-release of said compounds may also be beneficially employed.

One embodiment of this invention provides a method of decreasing rodent consumption of a liquid as compared to consumption of said liquid in the absence of a rodent repellent compound. In this method, said liquid is provided with at least one compound selected from the group comprising methyl anthranilate, ortho-aminoacetophenone, 2-methoxyacetophenone, 2-amino-4'5'-dimethoxyacetophenone, meta-aminoacetophenone, para-aminoacetophenone, ortho-methoxyacetophenone, meta-methoxyacetophenone and veratryl amine, in an amount which will provide a concentration of at least 1% weight/volume of said compound in said liquid.

Another embodiment of this invention provides a method of decreasing rodent consumption of a liquid as compared to consumption of said liquid in the absence of a rodent repellent compound. In this method, said liquid is provided with at least one compound selected from the group comprising acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, and para-methoxyacetophenone, in an amount which will provide a concentration of at least 0.5% weight/volume of said compound in said liquid.

Another embodiment provides a method of decreasing rodent consumption of feedlot as compared to consumption of said feedlot in the absence of a rodent repellent compound. In this method, said feedlot is provided with at least one compound selected from the group comprising acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone, and veratryl amine, in an amount effective to substantially reduce rodent consumption of said feedlot as compared to consumption of said feedlot in the absence of such compound. In this embodiment, the repellent compound may be provided in an emulsified form and applied to said feedlot or at least partially encapsulated in a solid vehicle and dispersed throughout said feedlot. Solid vehicles may include, for example, a modified starch, oil or polymer.

Rodent repellent compositions are also provided by this invention. Such compositions comprise at least one compound selected from the group comprising acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone, and veratryl amine, in an amount effective to repel rodents, and a suitable carrier.

Still another embodiment of this invention provides a method of reducing rodent predation, such as predation of trees. In this method, rodent repellent chemicals may be applied directly to the locus to be protected (e.g., trees) or to the surrounding area (e.g., rodent burrows).

one embodiment of this invention provides a method for decreasing rodent utilization of materials, for example, functional articles, as compared to utilization of said materials in the absence of a rodent repellent compound. In this method, said materials are provided with an effective repellent amount of a rodent repellent compound identified herein. It may be desirable to provide at least one repellent compound to containers for refuse, such as garbage cans, plastic bags, and boxes. This may be accomplished by coating an emulsified form of said compounds on the surfaces of such articles. Rodent repellency may also be provided by incorporating identified rodent repellent compounds into polymers for use in making functional articles such as refuse containers, packaging or covering materials used for items such as electrical cables.

In selecting a repellent compound, generally, amino substituents are more repellent than either methoxy or hydroxy substituents. There is generally no difference, however, between methoxy and hydroxy substituents in mammals. Although not wishing to be bound by any particular theoretical reasoning, these observations suggest that amino reactivity rather than basicity per se is the primary feature relating to repellency in mammals. There is little evidence to suggest that resonance contributed to repellency in mammals.

With reference to the foregoing, it will be appreciated that this invention provides materials and methods which can be used to effectively repel vertebrates, especially rodents, from consuming or utilizing materials otherwise susceptible to such consumption or utilization. Rodent repellent compositions are also provided. Various embodiments have been illustrated for the purpose of describing, but not limiting the invention. Other variations, within the scope of the invention, will occur to those of ordinary skill in the art.

EXAMPLES

Example 1

MATERIALS AND METHODS

Subjects—Seventy-two experimentally naive male CF-1 mice (*Mus musculus*) served as subjects. Animals were caged (27×21×14 cm) under a 12:12 light:dark cycle at 23 C and given free access to 8604-00 Wayne Rodent Blox. Chemicals—Five stimuli were selected: (1) methyl anthranilate (MA; CAS #134-20-3); (2) ortho-aminoacetophenone (OAP; CAS #551-93-9); (3) 2-amino-4'5'methoxyacetophenone (AMAP; CAS #4101-30-8); (4) 2-methoxyacetophenone (MAP; CAS #4079-52-1); and (5) veratryl amine (VA; CAS #5763-61-1). All 5 chemicals were NPLC grade and were obtained from Aldrich Chemical Company (Milwaukee, Wis.). Each was added to deionized/distilled water to yield saturated, emulsions with concentrations of 1.0% (weight/volume).

Procedure—Twelve mice (25–35 days old) were randomly assigned to each of 6 treatment groups, and adapted to an 18 hour water deprivation schedule. Adaptation was followed immediately by a 4 day pretreatment period. On each pretreatment day, all animals were given 3 hours access to tapwater in 10 ml syringes fitted with sipper tubes. At the end of the 3 hour period, ingestion was measured, and the mice were permitted an additional 3 hours ad libitum access to water. Water tubes were then removed from cages, and animals were deprived until the following day.

A 4 day treatment period immediately followed pretreatment. Treatment procedures were similar to those described for pretreatment, except that 5 groups were presented with their respective compounds in aqueous solution during the 3 hour measurement period. The sixth group continued to receive plain tapwater as a control.

Analysis—A 3-way analysis of variance (ANOVA) with repeated measures over periods (2 levels) and days (4 levels) was used to assess the results (Winer, *Statistical Principles in Experimental Design*, McGraw-Hill Inc., New York (1971)). Chemical (6 levels including the control group) was the independent factor in this analysis. In addition, for each chemical, a 2-way repeated measures ANOVA was used to test for period and day effects. In all cases, Tukey tests (See Winer, supra at page 201), were used to isolate differences among means ($P<0.05$).

Also tested, was whether intake of treated water differed from a theoretical value of zero ingestion. This analysis required a slight modification in calculation of the treatment sums of squares, wherein the grand mean was replaced by zero and the degrees of freedom reflected the number of treatments considered in the experiment. Estimates of the error term remained the same as in a standard ANOVA.
RESULTS Mice responded differently for each chemical across time (FIG. 1; F=4.5, df 12,165, P<0.001). Relative to the pretreatment period, intake of all chemicals declined (AMAP: F=194.26, df 1,11, P<0.001; MA: F=478.30, df 1,11 P<0.001; OAP: F=736.55, df 1,11, P<0.001; MAP: F=151.78, df 1,11, P<0.001; VA: F=442.91, df 1,11 P<0.001); with the exception of the control group, for whom intake during the pretreatment and treatment periods was equal (F=1.79; df 1,7; P=0.223). Intake of AMAP decreased across treatment days (F=2.88 df 3,33 P=0.051), while mice increased their intake of MA, MAP and VA (F=4.23, df 3,33 P=0.012, F=12.94, df 3,33 P<0.001, F=2.95, df 3,33, P=0.047; respectively). Ingestion of OAP and water (F=0.72, df 3,33 P=0.549, F=0.49, df 3,21, P=0.69; respectively) remained constant across days.

OAP was the only chemical which reduced intake to a level not significantly different from zero (F=4.34, df 1,11, P=0.061).

All 5 chemicals substantially reduced intake relative to pretreatment levels. MA, MAP and VA showed signs of habituation (i.e., animals ingested more of these substances on the last day than the first day of treatment). Intake of these chemicals on the last day of the treatment period, however, was still substantially below levels of water drank during the pretreatment period.

The most repellent material was OAP. This material effectively eliminated ingestion. Decreased ingestion of AMAP over time suggests that avoidance of this chemical involved learning. In other words, its effectiveness may depend partly on sensory factors and partly on food avoidance conditioning based on post-ingestional malaise.

Example 2

MATERIALS AND METHODS

Subjects—Two-hundred and twelve experimentally naive male CF-1 mice (*Mus musculus*) served as subjects. Animals were caged (27×21×14cm) under a 12:12 light:dark cycle at 23 C and given free access to 8604-00 Wayne Rodent Blox.
Chemicals—Acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone, isatoic anhydride, methyl cinnamate, methyl salicylate, phenethyl anthranilate and sodium benzoate were tested. Each chemical was added to deionized/distilled water to yield saturated, emulsions with concentrations of 0.50% (weight/volume). Ortho-aminoacetophenone, methyl anthranilate and 2-amino-4'5'-dimethoxyacetophenone, previously found to be effective at concentrations of 1.0% (w/v), were tried again at 0.5% (w/v).

Procedure—Mice (33–50 days old) were randomly assigned to each treatment group, and adapted to an 18 hour water deprivation schedule. Adaptation was followed immediately by a 4 day pretreatment period. On each pretreatment period, all animals were given 3 hours access to tapwater in 10 ml syringes fitted with sipper tubes. At the end of the 3 hour period, ingestion was measured, and the mice were permitted an additional 3 hours ad libitum access to water. Water tubes were then removed from cages, and animals were deprived until the following day.

A 4 day treatment period immediately followed pretreatment. Treatment procedures were similar to those described for pretreatment, except that groups were presented with their respective compounds in aqueous solution during their 3 hour measurement period.
RESULTS Chemicals that repelled mice at 0.50% (w/v) concentrations were acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone. Chemicals that did not repel mice were isatoic anhydride, methyl cinnamate, methyl salicylate, phenethyl anthranilate and sodium benzoate. Chemicals were listed as repellents if there was no overlap of 95% confidence intervals of the mean intake during pretreatment and treatment periods. Mean (se) intake during pretreatment and treatment periods and 95% confidence intervals for chemical are shown in FIGS. 2a–2w.

Example 3

MATERIALS AND METHODS

Subjects—24 prairie voles.
Chemicals—Ortho aminoacetophenone, 2-amino-4'5'-dimethoxyacetophenone, and methyl anthranilate were tested. Each chemical was added to deionized/distilled water to yield saturated, emulsions with concentrations of 0.50% (weight/volume).

Procedure—24 prairie voles were randomly assigned to each of 3 treatment groups, and adapted to an 18 hour water deprivation schedule. Adaptation was followed immediately by a 4 day pretreatment period. On each pretreatment day, all animals were given 3 hours access to tapwater in 10 ml syringes fitted with sipper tubes. At the end of the 3 hour period, ingestion was measured, and the mice were permitted an additional 3 hours ad libitum access to water. Water tubes were then removed from cages, and animals were deprived until the following day.

A 4 day treatment period immediately followed pretreatment. Treatment procedures were similar to those described for pretreatment, except that the 3 groups were presented with their respective compounds in aqueous solution during the 3 hour measurement period.
RESULTS All 3 chemicals substantially reduced intake relative to pretreatment levels. OAP reduced intake to a level not significantly different from zero. Average water intake (ml) by prairie voles during pretreatment and treatment periods are shown in FIG. 3.

Example 4

MATERIALS AND METHODS

Subjects—10 rats.
Chemicals—Ortho-aminoacetophenone was tested. OAP was added to deionized/distilled water to yield saturated, emulsions with concentrations of 0.50% (weight/volume).

Procedure—10 rats were adapted to an 18 hour water deprivation schedule. Adaptation was followed immediately by a 4 day pretreatment period. On each pretreatment day, all animals were given 3 hours access to tapwater in 10 ml syringes fitted with sipper tubes. At the end of the 3 hour period, ingestion was measured, and the rats were permitted an additional 3 hours ad libitum access to water. Water tubes were then removed from cages, and animals were deprived until the following day.

A 4 day treatment period immediately followed pretreatment. Treatment procedures were similar to those described for pretreatment, except that the rodents were presented with OAP in aqueous solution during the 3 hour measurement period.

RESULTS

OAP reduced average water intake (ml) to a level not significantly different from zero. Average water intake (ml) by rats during pretreatment and treatment periods are shown in FIG. 4.

Example 5

MATERIALS AND METHODS

Subjects—Two hundred and twenty four experimentally naive 30–35 day old male mice (*Mus musculus*) were caged (27×21×14 cm) under a 12:12 light:dark cycle (light onset at 0700) at 23 C, and given free access to 8604-00 Wayne Rodent Blox. Prior to testing, the animals were allowed free access to tapwater presented in 10 ml syringes fitted with sipper tubes. These same tubes were used during the experimental procedures described below.

Chemicals—Ortho-aminoacetophenone (CAS #551-93-9), meta-aminoacetophenone (CAS #99-03-6), para-aminoacetophenone (CAS #99-92-3), ortho-methoxyacetophenone (CAS #579-74-8), meta-methoxyacetophenone (CAS #586-37-8), para-methoxyacetophenone (CAS #100-06-1), ortho-hydroxyacetophenone (CAS #118-93-4); meta-hydroxyacetophenone (CAS #121-71-1) and para-hydroxyacetophenone (CAS #99-93-4) were obtained from Aldrich Chemical Company (Milwaukee, Wis.). Each moiety had a phenyl ring with an electron-donating primary amino, hydroxy, or methoxy group and an electron-withdrawing carbonyl group. The strength of donation was ranked as: amino >methoxy >hydroxy. Isomers of each moiety differed only in their substitution patterns on the phenyl ring.

Because acetophenones are generally insoluble in water, each compound was mixed in water under low heat to yield saturated emulsions with concentrations at 1.0% (mass/vol or vol/vol). Lower concentrations of 0.5 and 0.25% were prepared by serial dilution.

Procedure—Mice were randomly assigned to 28 treatment groups (n=8/group), and adapted to an 18 (1500 to 0900) hour water deprivation schedule. Adaptation was followed immediately by 4 days of pretreatment. On each pretreatment day, tapwater was presented at 0900 hours, and water intake between 0900 and 1200 was recorded. Between 1200 and 1500 hours, animals were provided ad libitum access to tapwater.

A 4 day treatment period immediately followed pretreatment. Treatment procedures were identical to those described for pretreatment, except that each group was given a different chemical and concentration during the 3 hour measurement period. A control group received plain water only.

Analysis—Initially, data for each chemical were evaluated separately in 3-factor analyses of variance (ANOVA) with repeated measures over periods and days. The independent factor in these ANOVAs was concentrations. Control group data were assessed in a 2-factor repeated measures analysis of variance in which the factors were periods and days.

Next, mean pretreatment and treatment drinking by each animal in each group were calculated. These means were assessed in separate 2-factor ANOVAs. The factors in these ANOVAs were chemicals and concentrations.

In all cases, Tukey honestly significant difference (HSD) tests (Winer, 1962:198) were used to isolate significant differences among means ($P>0.05$).

RESULTS

Analyses of Individual Chemicals

Figure 6:
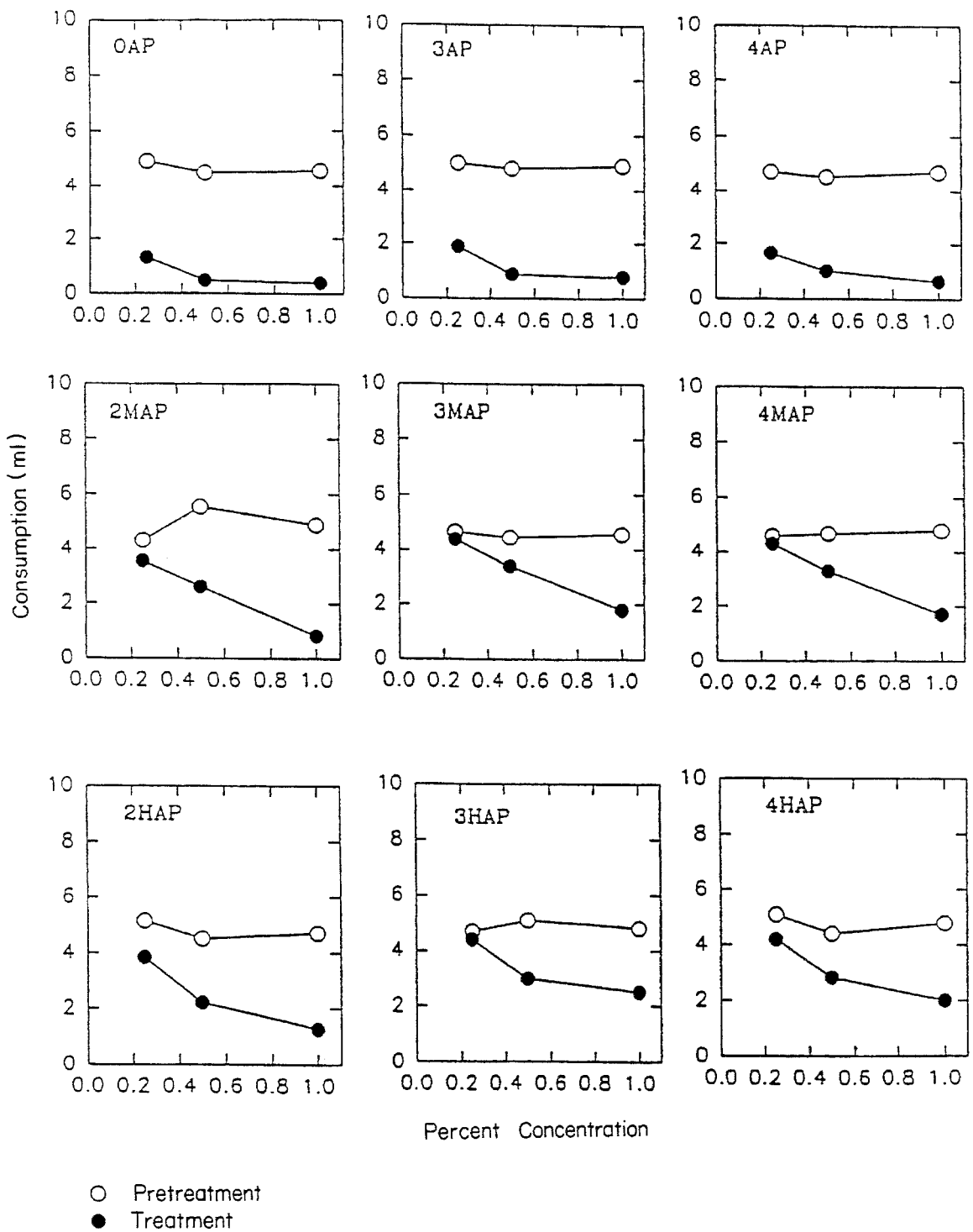
FIG. 6 is a series of graphs showing pretreatment (open circles) and treatment (darkened circles) consumption (in ml) of fluid containing ortho-aminoacetophenone (OAP), meta-aminoacetophenone (3AP), para-aminoacetophenone (4AP), ortho-methoxyacetophenone (2MAP), meta-methoxyacetophenone (3MAP), para-methoxyacetophenone (4MAP), ortho-hydroxyacetophenone (2HAP), meta-hydroxyacetophenone (3HAP), and para-hydroxyacetophenone (4HAP) in concentrations of 0.25%, 0.5% and 1.0% (mass/vol or vol/vol).

All analyses revealed differences between periods and with the exception of meta-aminoacetophenone and para-aminoacetophenone among concentrations (FIG. 5). Also, there were usually significant interactions between these terms. Post-hoc examination of these effects showed that pretreatment drinking was greater than treatment drinking and that differences in drinking between periods became greater as concentration increased (FIG. 6).

For meta-aminoacetophenone and para-aminoacetophenone, pretreatment drinking was greater than treatment drinking, but there were no other significant effects. All concentrations of these 2 chemicals produced strong avoidance responding.

Overall Analyses

Pretreatment—There were no significant differences among groups ($P<0.25$).

Treatment—There were significant differences among groups ($F=38.2$; 8,189df; $P<0.00001$). Post-hoc examination of this effect revealed 2 important patterns. First, amino substituents were significantly more repellent than the methoxy or hydroxy emulsions. There were no significant differences between the latter 2 substituent groups. Second, intramolecular hydrogen bonding appeared to be unimportant.

There were also significant differences among concentrations ($F=106.3$; 2,189df; $P<0.00001$). Not surprisingly, drinking was inversely related to concentration. Finally, the interaction between groups and concentrations was significant ($F=2.3$; 16,189df; $P<0.005$); amino substituents were superior repellents at lower concentrations than methoxy or hydroxy substituents.

Example 6

Four substances were evaluated. Two were predator urines; these typically inhibit foraging by a variety of rodents (Sullivan and Crump, 1986a; Sullivan and Crump, 1986b; Sullivan et al., 1988; Merkins et al., 1991; Swihart, 1991). The materials we evaluated, mink urine (MU) and coyote urine (CU), are aversive to mountain beavers in the laboratory (Epple et al., 1992). The third compound was ortho-aminoacetophenone (OAP) an effective repellent for mice (*Mus musculus*; Nolte et al., 1992), rats and voles (*Rattus norvegicus* and *Microtus ochrogaster*; Nolte, unpublished data). The fourth substance was denatonium benzoate (DB), an extremely bitter substance.

MATERIALS AND METHODS

Subjects—Mountain beavers were captured in the Capitol State Forest in Grays Harbor County, approximately 20 miles from the Denver Wildlife Research Center (DWRC) field station in Olympia, Wash. Animals were housed in outdoor pens (3×3 m) with a nest box in the center of each pen. Throughout trials, animals were given free access to water and food pellets (X-Cell Feed Company, Tacoma, Wash.).

Compounds—Hawthorne's mink and coyote urine were purchased from M&M Furs Company (Bridgewater, S. Dak.). OAP (CAS #551-93-9) was obtained from Aldrich Chemical Company (Milwaukee, Wis.) and DB (CAS

3734-33-6) was donated by Atomergic Chemicals (Farmingdale, N.Y.). OAP and DB were mixed with water to yield 1.0% (mass/mass) emulsions/solutions.

Vegetation—Five leaf segments of salal (approx. 25 cm) were collected near the DWRC Olympia field station. Douglas fir seedlings (approx. 20 cm) grown 2 years in nursery seed beds were clipped at ground level. On collection, individual stems of both species were placed in plastic Aqua Piks (Syndicate Sales Inc., Kokomo, Ind.).

Salal and Douglas fir were individually submerged in 1 of 5 treatments: 1) MU; 2) CU; 3) 1.0% emulsion of OAP; 4) 1.0% solution of DB; or 5) water (control). All samples were allowed to air dry before they were offered to mountain beaver.

Procedure—Seven mountain beavers were each offered 20 treated Douglas fir seedlings. Seedlings from each of the 5 treatments were randomly located within 4 blocks. Treatments within blocks were placed in a row approximately 10 cm apart. Blocks were located along pen walls about 1.5 m from the nest box. Treatment efficacy was evaluated by counting the number of clipped seedlings after 2 weeks.

Subsequently, a similar trial was conducted with salal. Eighteen mountain beaver (7 used in the above trial) were each given 20 treated salal plants as described above. Treatment efficacy was evaluated by counting the number of missing leaves after 48 hours. One animal was eliminated from the study because it failed to meet study criteria of taking at least 1 leaf.

Analysis—One-way analyses of variance were used to assess treatment effects (Winer 1971). Subsequent to the omnibus procedures, Tukey tests (Winer 1971:201) were used to isolate differences among means (P<0.05).

RESULTS

Figure 7:
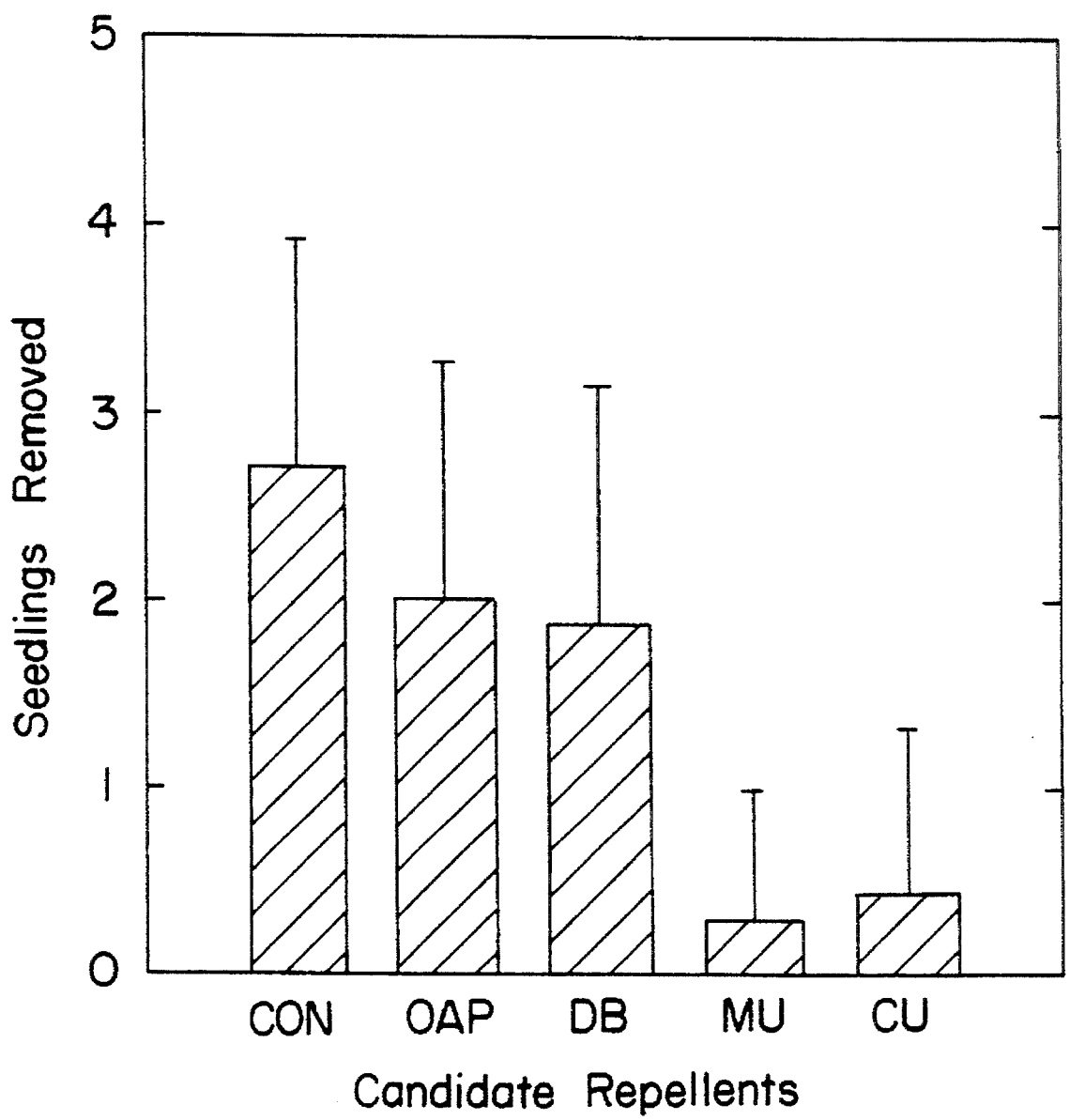
FIG. 7 is a graph showing the mean number of Douglas fir seedlings treated with water (CON), ortho-aminoacetophenone (OAP), denatonium benzoate (DB), mink urine (MU) or coyote urine (CU) that were clipped by mountain beaver during a two week trial. Vertical bars are ±SE.
Figure 8:
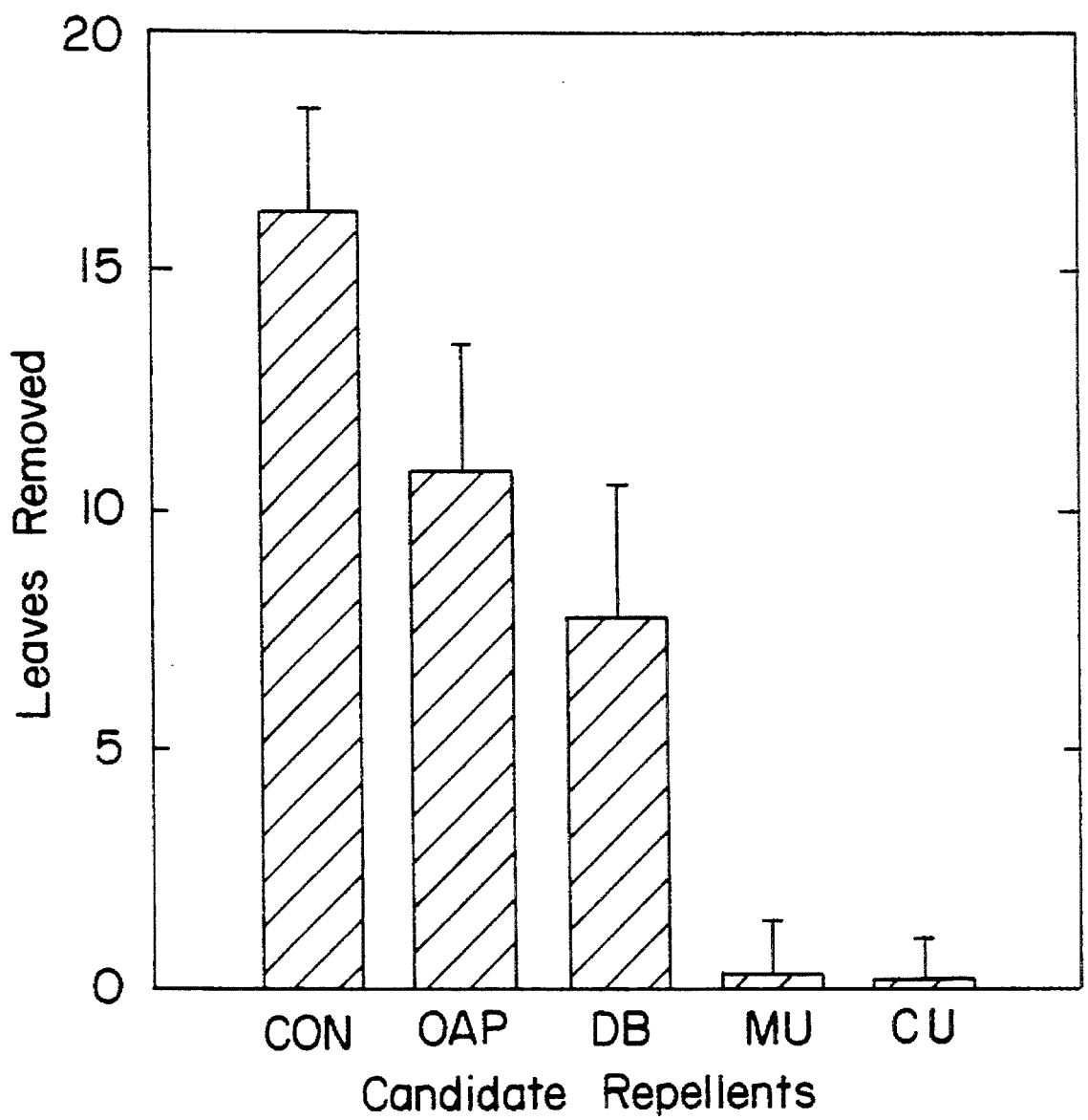
FIG. 8 is a graph showing the mean number of salal leafs treated with water (CON), ortho-aminoacetophenone (OAP), denatonium benzoate (DB), mink urine (MU) or coyote urine (CU) that were taken by mountain beaver during a 48 hour trial. Vertical bars are ±SE.

There were differences among treatments for both Douglas fir seedlings and salal (F=4.6, 4, 34, P=0.0057; F=30.795, 4, 84, P<0.0001; respectively). In treatments on Douglas fir, both predator urines reduced damage relative to water treated control seedlings (FIG. 7). Neither OAP or DB produced significant reductions in damage. In treatments on salal, all 4 candidate repellents reduced damage, but both predator urines were significantly more effective than either OAP or DB (FIG. 8).

DISCUSSION AND MANAGEMENT IMPLICATIONS

All treatments reduced mountain beaver damage relative to controls. Efficacy of treatments was similar whether they were used to treat Douglas fir or salal. Mountain beavers clipped fewer plants treated with either of the predator urine than they did plants treated with OAP or DB.

Mountain beavers did not habituate to mink or coyote urine over the 2 week trial period. These sustained effects are consistent with results collected for other species. Woodchucks avoid gnawing fruit trees sprayed with bobcat urine for as long as 93 days (Swihart, 1991). Further, woodchucks continued to avoid bobcat urine even when exposed to the odor in consecutive years (Swihart, 1991).

Example 7

MATERIALS AND METHODS

Wires treated with ortho-aminoacetophenone, methyl anthranilate, 2-amino-4'5'-dimethoxyacetophenone, veratryl amine and 2-methoxyacetophenone suffered less damage than untreated wires. Wires were treated with a topical coating of 1.0% solutions of the above compounds. A sixth group was coated with plain water. Treated wires were placed with mice for 48 hours. All compound treatments reduce damage relative to the water treatment. Wires treated with ortho-aminoacetophenone suffered the least damage.

We claim:

1. A method of repelling rodents from a material susceptible to rodent predation selected from the group consisting of crops, seeds, seedlings, telephone cables, electric cables, and refuse containers comprising the steps of:

(a) selecting at least one rodent aversive compound from the group consisting of acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone, 2-methoxyacetophenone, and veratryl amine; and (b) applying said rodent aversive compound selected in step (a) to said material otherwise susceptible to rodent predation in an amount effective to repel said rodent from said material.

2. A method of repelling rodents from a liquid susceptible to rodent utilization or consumption, comprising the steps of:

(a) selecting at least one rodent aversive compound from the group consisting of methyl anthranilate, ortho-aminoacetophenone, 2-methoxyacetophenone, 2-amino-4'5'-dimethoxyacetophenone, meta-aminoacetophenone, para-aminoacetophenone, ortho-methoxyacetophenone, meta-methoxyacetophenone and veratryl amine; and (b) introducing said at least one compound into said liquid in an amount which provides a concentration of at least 1% weight/volume of said compound in said liquid.

3. The method of claim 2 wherein said compound is ortho-aminoacetophenone.

4. A method of repelling rodents from a liquid susceptible to rodent utilization or consumption comprising the steps of:

(a) selecting at least one rodent aversive compound from the group consisting of acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, and para-methoxyacetophenone; and (b) introducing said at least one compound into said liquid in an amount which provides a concentration of at least 0.5% weight/volume of said compound in said liquid.

5. The method of claim 4 wherein said compound is ortho-aminoacetophenone.

6. A method of repelling rodents from a liquid susceptible to rodent utilization or consumption comprising the steps of:

(a) selecting at least one rodent aversive compound from the group consisting of ortho-aminoacetophenone, meta-aminoacetophenone, para-aminoacetophenone, ortho-methoxyacetophenone and meta-methoxyacetophenone; and (b) introducing said at least one compound into said liquid in an amount which provides a concentration of at least 0.25% weight/volume of said compound in said liquid.

7. The method of claim 6 wherein said compound is ortho-aminoacetophenone.

8. The method of claim 1 wherein step (b) further comprises providing at least one of said compounds in an emulsified form and coating said material with said at least one compound.

9. The method of claim 1 wherein step (b) further comprises providing at least one of said compounds at least partially entrapped in an inert solid vehicle and dispersing said inert solid vehicle throughout said material.

10. A method of repelling rodents from an article comprising a polymer wherein said article is susceptible to rodent predation comprising the steps of:
   (a) selecting at least one compound from the group consisting of acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone and veratryl amine; and
   (b) incorporating an effective rodent repellent amount of said compound into said polymer for use in making said article.

11. A method of repelling rodents from a locus susceptible to rodent utilization comprising the steps of:
   (a) selecting at least one compound from the group consisting of acetophenone, 2-aminobenzyl alcohol, 2-amino-4'5'-dimethoxyacetophenone, anthranilamide, anthranilic acid, isobutyl anthranilate, 4-ketobenztriazine, meta-aminoacetophenone, meta-hydroxyacetophenone, meta-methoxyacetophenone, 2-methoxybenzoic acid, methyl anthranilate, ortho-aminoacetophenone, ortho-hydroxyacetophenone, ortho-methoxyacetophenone, para-aminoacetophenone, para-hydroxyacetophenone, para-methoxyacetophenone and veratryl amine; and
   (b) providing said compound in the vicinity of said locus in an amount and distribution sufficient to repel said rodents from said locus.

12. The method of claim 11 wherein step (b) further comprises providing said at least one of said rodent aversive compounds to said locus in an emulsified form wherein said at least one compound is mixed with a liquid diluent to provide a 1.0% mass/mass emulsion.

13. The method of claim 11 wherein said compound is ortho-aminoacetophenone.

14. The method of claim 11 wherein said locus is a tree.

15. A method of reducing predation of a locus by rodents comprising the steps of:
   (a) selecting at least one rodent aversive compound from the group consisting of ortho-aminoacetophenone and denatonium benzoate; and
   (b) providing said rodent aversive compound in the vicinity of said locus in an amount and distribution sufficient to reduce the rodent predation within said locus.

16. The method of claim 15 wherein said compound is ortho-aminoacetophenone.

17. The method of claim 15 wherein step (b) further comprises providing said at least one of said rodent aversive compounds in the vicinity of said locus in an emulsified form wherein said at least one compound is mixed with a liquid diluent to provide a 1.0% mass/mass emulsion.

18. The method of claim 15 wherein said compound is ortho-aminoacetophenone.

19. The method of claim 15 wherein said area in the vicinity of said locus is the area immediately in or adjacent to a rodent burrow.

20. A method of repelling rodents from a material susceptible to rodent predation comprising the steps of:
   (a) selecting at least one rodent aversive compound from the group consisting of anthranilic acid, meta-hydroxyacetophenone, methyl anthranilate, para-aminoacetophenone, and ortho-hydroxyacetophenone; and
   (b) entrapping said compound selected in step (a) in an inert solid vehicle; and
   (c) dispersing said inert solid vehicle throughout said material in an amount and distribution effective to repel said rodents from said material.

21. The method of claim 20 wherein said material is a crop.

22. A method of protecting articles from utilization by rodents comprising providing methyl anthranilate to said article in an amount and distribution sufficient to repel said rodents from said article.

23. The method of claim 22 wherein said methyl anthranilate is provided in a 1.0% emulsion and provided to said article by coating said article with said emulsion.

* * * * *